United States Patent [19]

Fabinski et al.

[11] Patent Number: 5,340,542
[45] Date of Patent: Aug. 23, 1994

[54] APPARATUS FOR THE MEASUREMENT OF THE TOTAL CONTENT OF ORGANIC CARBON AND NITROGEN IN WATER

[75] Inventors: Walter Fabinski, Kriftel; Peter Hübschmann, Nidderau; Peter Schlau, Frankfurt; Christian Wolff, Karben, all of Fed. Rep. of Germany

[73] Assignee: Hartmann & Braun Aktiengesellschaft, Frankfurt am Main, Fed. Rep. of Germany

[21] Appl. No.: 71,106

[22] Filed: Jun. 4, 1993

Related U.S. Application Data

[62] Division of Ser. No. 880,576, May 8, 1992, Pat. No. 5,292,666.

[30] Foreign Application Priority Data

May 10, 1991 [DE] Fed. Rep. of Germany ........ 4115425

[51] Int. Cl.$^5$ ...................... G01N 21/00; G01N 33/00
[52] U.S. Cl. ................... 422/82.05; 436/114; 436/116; 436/145; 436/146; 250/344
[58] Field of Search ............... 436/116, 114, 145, 146; 422/82.05; 250/344

[56] References Cited

U.S. PATENT DOCUMENTS

| | | | |
|---|---|---|---|
| 3,880,587 | 4/1975 | Szakasits et al. | 422/68 |
| 4,066,402 | 1/1978 | Komigama et al. | 436/146 |
| 4,271,124 | 6/1981 | Specter | 422/68 |
| 5,055,688 | 10/1991 | Fabinski | 250/344 |
| 5,081,047 | 1/1992 | Steele et al. | 436/146 |
| 5,246,868 | 9/1993 | Busch et al. | 436/101 |

Primary Examiner—Nina Bhat
Attorney, Agent, or Firm—Horst M. Kasper

[57] ABSTRACT

The invention relates to a method for measuring of the total content of organic carbon and of nitrogen in water. The total organic carbon value is obtained correctly as the sum of the liquid, dissolved, and solid materials of a sample of the water. The device comprises a non-dispersive infrared (NDIR) gas analyzer for the simultaneous measurement of the concentration of the gas components carbon dioxide $CO_2$ and nitrogen oxide NO. The NDIR gas analyzer includes a phase separator (50), a thermal reactor (52), a double cooler (70), two valves (54, 56), as well as two amplifiers (58, 60) for the pneumatic signals of the receiver detectors (30, 36) with a display (62. 64) for the measured concentrations, total organic carbon and total nitrogen. The sample is split in a phase separator (50) into a gaseous and into a liquid part. The gaseous part, which comprises substantially the inorganic part of the carbon, the total inorganic carbon part in the form of carbon dioxide $CO_2$ gas, is cooled in a cooler to such an extent that a substantial part its water vapor content is deposited in the cooler by condensation. The dried gaseous part is led as comparison gas through the comparison cuvette. This step serves to compensate the total inorganic carbon part of the sample and to compensate for unavoidable water vapor cross-sensitivities during the measurement of the carbon dioxide $CO_2$ concentration and of the nitrogen oxide NO concentration.

7 Claims, 2 Drawing Sheets

APPARATUS FOR THE MEASUREMENT OF THE TOTAL CONTENT OF ORGANIC CARBON AND NITROGEN IN WATER

This application is a divisional of Ser. No. 07/880,576 filed May 8, 1992 now U.S. Pat. No. 5,292,666.

BACKGROUND OF THE INVENTION

1. Field of the Invention

The invention relates to a method for the measurement of the total content of organic carbon and of nitrogen in water, where a sample, taken from the water to be investigated and analyzed, is evaporated, wherein the organic carbon is oxidized to carbon dioxide, wherein the nitrogen is oxidized to nitrogen oxide in a thermal reactor, and wherein the measurement is performed based on the gas sample, formed from the sample containing carbon dioxide $CO_2$ and nitrogen oxide NO.

2. Brief Description of the Background of the Invention Including Prior Art

The following abbreviations will be used in the following:

- TOC = total organic carbon, indicating the total carbon present in the water to be measured in the form of organic compounds.
- TIC = total inorganic carbon, indicating the total carbon in the form of inorganic compounds present in the water to be measured.
- TC = total carbon, indicating the total carbon present in the water to be measured.

The organic part of carbon of the total organic carbon (TOC), is an oxygen consuming user and thus of interest in the determination of the chemical composition of waters. The German Industrial Standard 38 409 (H) provides a basis for the determination of the total organic carbon (TOC) value.

The German Industrial Standard 38,409 (H) corresponds to the proposed International Standard ISO/DS 8245, submitted on Jan. 16, 1986 and defines the designations TC=total carbon, TIC=total inorganic carbon and TOC=total organic carbon.

TN = total nitrogen, indicating the total amount of nitrogen present in the water to be measured. The designation TN is defined in the proposed German Industrial Standard DIN 38,409, part 27.

Frequently, only a part, i.e., the part of the dissolved total organic carbon (TOC) is captured in practical situations instead of the correct values. Frequently, also volatile organic components can be present in water, which are lost during the separation of the sample of inorganic compounds. Thus, the total organic carbon (TOC) value, is not completely captured with such a method.

The part of bonded nitrogen, total nitrogen (TN), is of interest in addition to the total organic carbon (TOC) value. The total nitrogen (TN) value gives an indication relative to the load of the water with nitrogen compounds derived from natural and industrial discharges. A proposal for the measurement of the total nitrogen (TN) is given in the proposed German Industrial Standard 38 409, part 27.

Total organic carbon (TOC) determinations are known. The total carbon (TC) and the total inorganic carbon (TIC) are measured and the total organic carbon (TOC) is determined by difference formation, compare for example German Printed Patent documents DE-OS 2,811,135 (equivalent U.S. Pat. No. 4,217,108), DE-OS 2,458,143 (equivalent U.S. Pat. No. 3,854,881), DE-OS 2,322,293 (equivalent U.S. Pat. No. 3,814,583), and European Patent document EP-PS 0,150,923 (equivalent U.S. Pat. Nos. 4,626,413, 4,666,860, 5,047,212).

A method for the continuous and quantitative determination of organic and inorganic carbon compounds in water is taught in the German Printed Patent document DE-OS 3,909,240, wherein the water to be analyzed is acidified in a degasification vessel. A transport gas flow is fed through the water into the degasification vessel. Water and transport gas pass from the degasification vessel into a decomposition reactor. The carbon dioxide $CO_2$ content of the transport gas is determined downstream of the degasification container or downstream of the decomposition reactor. The parts of organic and inorganic carbon compounds are separated from each other or are determined as a sum.

F. Ehrenberger teaches in the paper entitled "For the determination of the oxygen requirement values and carbon characterizing values in the water quality determination", GIT Fachz. Lab. 23, Voluble 8/79, pages 738 through 747, several methods for the determination of total organic carbon (TOC), where the methods are based on wet chemical or thermal reaction of the organic content materials and on the quantitative oxidation of the organically bonded carbon to carbon dioxide. The carbon dioxide $CO_2$ content is determined by a chemical or physical method. A simultaneous determination of nitrogen is not provided for in the methods described by F. Ehrenberger.

A value obtained by a total nitrogen (TN) auxiliary measurement is added in individual cases to a value of a total organic carbon (TOC) measurement by furnishing of a corresponding analyzer as set forth in the German Printed Patent Document DE-OS 2,621,616 and in the equivalent U.S. Pat. No. 4,066,402. This method is expensive and generates undesirable delay times of the display. Frequently, the calibration is performed manually with a high-purity zero-conductivity water for the zero point establishment and with a calibration solution for establishing the sensitivity. In addition, measurement errors caused by the principle of the method are accepted. Thus, deviations from the predetermined sensitivity occur if a base load of carbon dioxide $CO_2$ becomes changed.

The German Printed Patent document DE-OS 2,621,616 to Yoshiki Komiyama teaches an analytical method and device for the determination of the total nitrogen and/or carbon contents in aqueous solutions which contain nitrogen and/or carbon containing material.

The German Printed Patent document DE-OS 3,937,141 to Walter Fabinski, having an equivalent U.S. Pat. No. 5,055,688, teaches a non-dispersive infrared gas analyzer for the simultaneous measurement of the concentration of several components of a gas sample. The NDIR gas analyzer is suitable for the determination of the two gas components, carbon dioxide and nitrogen oxide. An analyzer is connected to and receives signals from the receiver detectors. A control and display unit is connected to the analyzer.

The reference M. Ascherfeld et al. in "Technisches Messen—tm", Volume 57/1990, Issue 1, pages 11–17, teaches "Expanded Possibilities and Applications with the NDIR Photometer Uras 10E".

The German Patent 2,105,307 to Theodor Bilichnianski teaches a liquid dispenser for feeding of reagents to an automatically operating apparatus for the continuous analysis of samples.

The German Patent DE-3,640,718 C2 to Willi Apel et al. teaches a membrane capacitor for measuring of very small pneumatic alternating pressures.

The German Printed Patent document DE-OS 3,909,240 A1 to Hans Duve teaches a method for the determination of disintegratable carbon compounds in water.

SUMMARY OF THE INVENTION

1. Purposes of the Invention

It is an object of the present invention to provide a method for the simultaneous measurement of the total organic carbon (TOC) content and of the total nitrogen (TN) content in water, which captures the dissolved as well as the volatile components, which method considers zero point shiftings and sensitivity changes based on carbon dioxide $CO_2$ changes during the total organic carbon (TOC) measurement as well as cross-sensitivities versus water vapor components during the total nitrogen (TN) measurement, and which allows a zero point calibration without using zero water.

It is another object of the present invention to provide a method which allows an accurate and simultaneous determination of bound nitrogen and of organic bound carbon in a water-containing liquid.

It is yet another object of the present invention to furnish a method for the determination of organic bound carbon and for the determination of bound nitrogen in water, which method is substantially automatic and does not require separate analytical methods.

These and other objects and advantages of the present invention will become evident from the description which follows, 2. Brief Description of the Invention According to the present invention, there is provided for a method for a determination of the total content of organic carbon and of nitrogen in an aqueous fluid sample comprising the following steps. An inorganic carbon dioxide part is separated from a sample with the aid of a phase separator, wherein the inorganic dioxide part is loaded with water vapor. The inorganic carbon dioxide part is passed through a first cooler. The inorganic carbon dioxide part coming from the first cooler is used as comparison gas. The inorganic carbon dioxide part is fed to a comparison cuvette. The inorganic carbon dioxide part coming from the comparison cuvette is fed to a first input of a thermal reactor. A remaining sample from the phase separator is fed to a second input of the thermal reactor. The carbon part present in the sample is oxidized to carbon dioxide, and the nitrogen part present in the sample is oxidized to nitrogen oxide in the thermal reactor. The oxidized sample obtained is loaded into a second cooler having the same temperature as the first cooler. The oxidized sample is saturated with a water vapor of a partial pressure corresponding to a water vapor saturation at the same temperature as the temperature of water vapor saturation in the comparison gas. The oxidized sample coming from the second cooler is fed as a measurement gas to a measurement cuvette. The measurement gas contains the total carbon dioxide part and the total nitrogen oxide part of the gas sample. The comparison cuvette and the measurement cuvette are adjacently disposed cuvettes. The comparison gas with the actual inorganic carbon dioxide part is fed simultaneously through the measurement cuvette and the comparison cuvette for taking into consideration the inorganic carbon dioxide $CO_2$ part, which is present as an interfering background in the sample. The measurement is performed on the basis of the gas sample, containing carbon dioxide $CO_2$ and nitrogen oxide NO formed by the sample. A modulated light beam generated by an infrared radiator is passed through the comparison cuvette and through the measurement cuvette. A light beam emanating from the comparison cuvette is directed onto a first section of a first receiver detector disposed behind the comparison cuvette. A light beam emanating from the measurement cuvette is directed onto a second section of the first receiver detector disposed behind the measurement cuvette. A first pneumatic signal is generated in the first receiver detector. Said first pneumatic signal corresponds to the difference of the total carbon part and of the inorganic carbon part and thus corresponds to the organic carbon part of the sample. The first pneumatic signal generated in the first receiver detector is amplified with a first electronic amplifier. The light beach emanating from the first receiver detector is filtered through a radiation filter disposed following the first receiver detector. The radiation filter is transparent to the light beams in a region of radiation absorption of the component nitrogen oxide NO of the sample. A second pneumatic signal is generated in a second receiver detector sensitized to nitrogen oxide. The second receiver detector exhibits two chambers. The two chambers in each case are filled with the same gas component to be determined of the sample. The second pneumatic signal generated in the second receiver detector is amplified with a second electronic amplifier. Said second pneumatic signal corresponds to the difference of the water vapor loaded nitrogen oxide part of the measurement gas and of the water vapor part of the comparison gas and thus to the total nitrogen part of the sample.

A non-dispersive infrared gas analyzer can be employed for the simultaneous measurement of the components carbon dioxide and nitrogen oxide in the sample. The inorganic carbon dioxide part coming from the comparison cuvette can be fed to a first valve. The inorganic carbon dioxide part from a first output of the first valve can be fed to a first input of a thermal reactor. A liquid sample can be fed from the phase separator through a second input to the thermal reactor. The two chambers of the first receiver detector can be disposed successively as seen in beam direction.

A calibration cuvette having a first chamber filled can be furnished with a neutral gas in a path of the comparison beam and can have a second chamber filled with a calibration gas in a path of the measurement beam for setting the sensitivity of the gas analyzer for the gas components carbon dioxide $CO_2$ and nitrogen oxide NO to be measured. There can be set in a first step a zero point of the non-dispersive infrared gas analyzer for the total organic carbon value and the total nitrogen value. The first chamber of the calibration cuvette can be slid into a beam path between the first cuvette and the first receiver detector, and the second chamber of the calibration cuvette can be slid between the second cuvette and the second receiver detector. The sensitivity of the first amplifier can be set for the present inorganic carbon dioxide concentration. The sensitivity of the second amplifier can be set simultaneously with the setting of the sensitivity of the first amplifier for determining a nitrogen oxide concentration. The comparison gas can be fed to the comparison cuvette after termination of the setting processes for the zero point and for the sensitivity. The measurement gas can be fed to the measurement cuvette after termination of the setting processes for the zero point and for the sensitivity.

The steps for the setting of the zero point and of the sensitivity of the gas analyzer can be repeated at predetermined time intervals for a continuous consideration of the inorganic carbon dioxide part in the sample.

A connection to the measurement cuvette can be furnished in a return line from the comparison cuvette to the thermal reactor such that the comparison gas flows through the comparison cuvette and through the measurement cuvette upon actuation of a first valve. A discharge of the measurement gas from the reactor can be furnished in the feed line of the measurement gas to the measurement cuvette in front of or behind the double cooler upon actuation of a second valve. An actuation of the first valve and of the second valve can be performed during the setting of the zero point and of the sensitivity of the gas analyzer.

The measurement can be performed with a calibration liquid including materials for total organic carbon and total nitrogen analysis as sample for calibrating, wherein the following calibration steps are performed. The zero point and the sensitivity of the first amplifier and of the second amplifier can be set during the following above recited steps. The comparison gas with the actual inorganic carbon dioxide part can be fed simultaneously through the measurement cuvette and the comparison cuvette for taking into consideration the inorganic carbon dioxide $CO_2$ part, which is present as an interfering background in the sample. According to a first step the zero point of the non-dispersive infrared gas analyzer for the total organic carbon value and the total nitrogen value can be set, and according to a second step, the calibration cuvette can be slid into the beam path. The sensitivity of the first amplifier can be set for the present inorganic carbon dioxide concentration and simultaneously the sensitivity of the second amplifier can be set for the nitrogen oxide concentration. The measurement gas can be fed to the measurement chamber and the comparison gas can be fed to the comparison chamber after termination of the setting processes for the zero point and for the sensitivity. The first valve and the second valve can be deactivated and the sensitivity of the first amplifier and of the second amplifier can be set for the concentration values for total organic carbon and total nitrogen, predetermined by the calibration liquid.

A sample of the water to be analyzed is fed to a phase separator, which is frequently called stripper, where the sample is split up into a gaseous and a liquid part. The gaseous part, which contains substantially the inorganic part of carbon, which contains the total inorganic carbon (TIC) part in the form of carbon dioxide $CO_2$ gas and in part also carbon components in the form of easily volatile hydrocarbon compounds, is cooled in a cooler to a temperature of about 4° C. to such an extent that a predominant part of a water vapor content present is deposited in the cooler by condensation. The thus dried gaseous part passes as a comparison gas into a comparison cuvette of a non-dispersive infrared (NDIR) gas analyzer operating according to the material comparison method. This step serves to compensate the total inorganic carbon (TIC) part of the sample and to compensate the unavoidable water vapor cross-sensitivity during the measurement of the carbon dioxide $CO_2$ concentrations and of the nitrogen oxide (NO) concentrations. The gaseous part, exiting out of the comparison cuvette, is completely returned to the liquid part of the sample and is oxidized together with the liquid part of the sample in a thermal reactor. The oxidation of the sample is performed both for the volatile part of carbon as well as for the carbon part dissolved in water to give carbon dioxide $CO_2$ and for the nitrogen part to give nitrogen oxide (NO).

The water vapor is separated from the thus obtained gas sample, which gas sample contains the total carbon part and the total nitrogen part of the sample, in the cooler by condensation at the same temperature as the temperature of the comparison gas and the gas sample is fed as a measurement gas to the measurement cuvette of the NDIR gas analyzer. A pneumatic signal is generated in the first receiver sensitized to carbon dioxide $CO_2$, where the pneumatic signal corresponds to the concentration value of total carbon (TC) minus total inorganic carbon (TIC) and thus to the desired total organic carbon (TOC) value. A pneumatic signal is generated in the subsequently disposed receiver sensitized to nitrogen, where the pneumatic signal corresponds to the difference obtained from the water-vapor-loaded nitrogen oxide (NO) part of the measurement gas and of the water vapor part of the comparison gas, i.e., the desired nitrogen part (TN) in the sample.

The gas sample taken from the phase separator is led both through the measurement channel as well as through the comparison channel for balancing the zero point and the sensitivity of the analyzer. Zero point shiftings of the amplifiers disposed downstream of the receivers, based on carbon dioxide $CO_2$ offset changes or based on water $H_2O$ parts causing the cross-sensitivity, as well as aging and soiling of the gas analyzer are balanced with this adjustment setting. Finally, the end point of the two amplifiers is set to the concentration values by sliding a calibration cuvette into the beach path between the cuvettes and the receivers, where the concentration values are predetermined by the test gas enclosed in the calibration cuvette. This balancing method assures that also small measurement regions can be realized with sufficient stability. In addition, this balancing method can be performed based on gas stored in storage bottles and under elimination of a requirement for use of external calibration gases.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

DESCRIPTION OF INVENTION AND PREFERRED EMBODIMENTS

Figure 1:
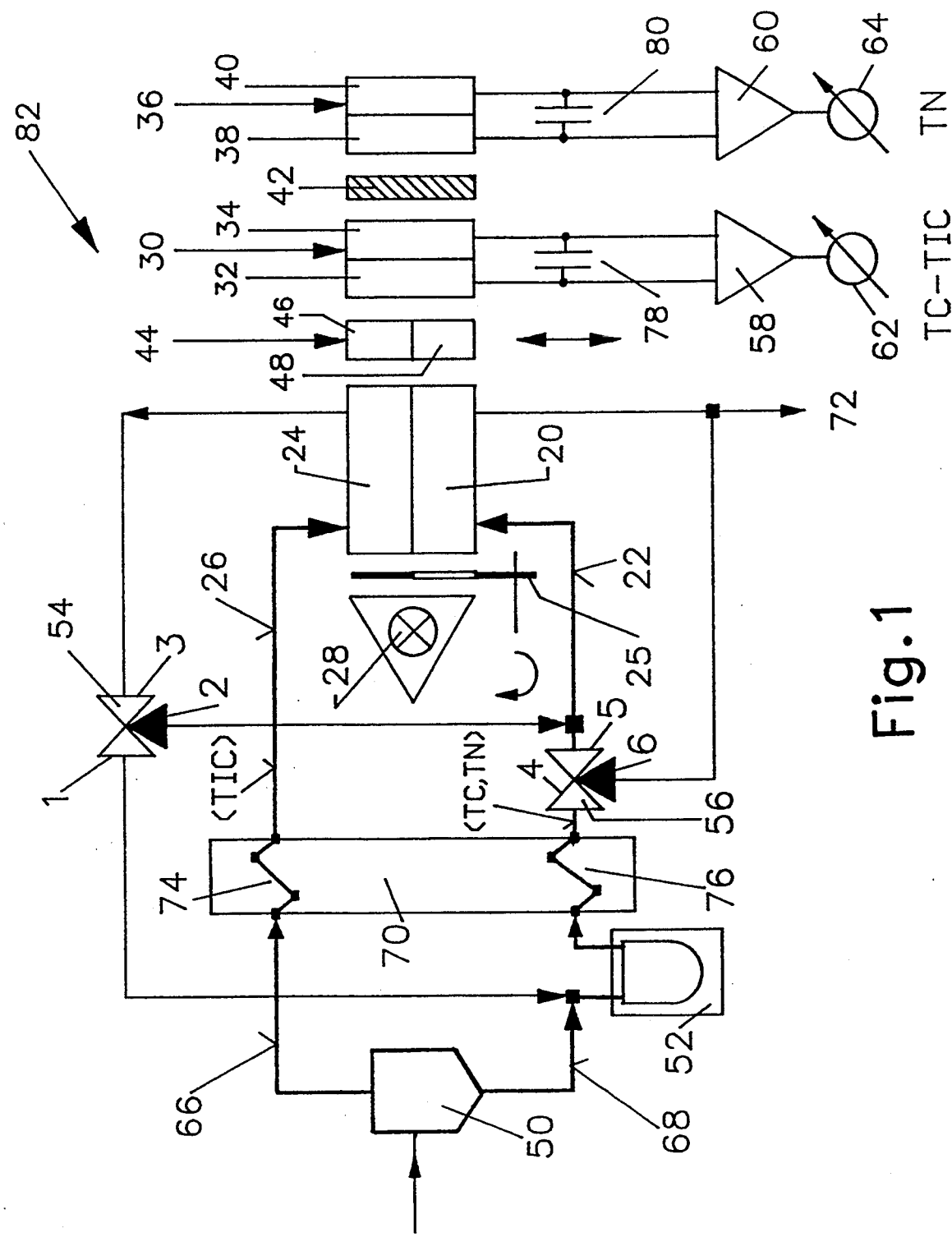
FIG. 1 shows a schematic diagram of a method for measuring the total content of organic carbon and of nitrogen in water.

The invention device includes a phase separator 50, a thermal reactor 52, a double cooler 70 having a first cooler and a second cooler 76, two paths 74, 76, and two valves 54 and 56.

A cooler can be provided by a conventional and commercially available gas cooler. The reference paper GIT shows on page 743, in FIG. 11, an apparatus with a cooler, where the cooler is disposed downstream of a thermal reactor.

The reference paper GIT describes on page 739, Section C, two methods for the separation of the total inorganic carbon TIC part out of an aqueous sample. The phase separator 50 of the present application operates according to the degasification method described in the reference paper GIT. A phase separator can also be called a stripper or a sparger.

The reference German Printed Patent document DE-AS 2,260,295 and U.S. Pat. No. 3,703,355 show in FIG. 1 an evaporation chamber 12, which operates as a phase separator, wherein the inorganic carbon parts, present in a sample, such as carbonate, bicarbonate are transferred into carbon dioxide $CO_2$ and are driven out from an aqueous sample by the addition of inorganic acids.

The invention device comprises a known non-dispersive infrared (NDIR) gas analyzer for the simultaneous measurement of the concentration of the gas components carbon dioxide $CO_2$ and nitrogen oxide NO, with two adjacently disposed cuvettes, the measurement cuvette 20 for the measurement gas 22 and the comparison cuvette is 24 for the comparison gas 26. The measurement cuvette 20 and the comparison cuvette 24 are passed by modulated light beams of an infrared radiator 28, wherein the light beams fall onto pneumatic receiver detectors 30 and 36 after partial absorption in the measurement cuvette 20 and the comparison cuvette 24 and in the calibration cuvette 44. A chopper wheel 25 is disposed between the infrared radiator source 28 and the comparison cuvette 24 and the measurement cuvette 20 for providing light modulation. The receiver detectors 30 and 36 exhibit in each case two chambers 32, 34; 38, 40 disposed in series in beam direction, wherein the two chambers 32, 34; 38, 40 in each case are filled with one of the components to be determined of the gas sample and, in fact, the receiver detector 30 with the component carbon dioxide $CO_2$ and the receiver detector 36 with the component nitrogen dioxide NO.

A radiation filter 42 is disposed between the receiver detectors 30 and 36. The radiation filter 42 is transparent to the light beams in the region of the radiation absorption of the component nitrogen oxide NO of the gas sample. In addition, a calibration cuvette 44 with two adjacently disposed chambers 46, 48 can be slid into the beam path between the measurement cuvette 20 and the comparison cuvette 24 and the first receiver detector 30. The chambers 46, 48 of the calibration cuvette 44 are filled with a calibration gas, for example, with carbon dioxide $CO_2$ and/or nitrogen oxide NO in the measurement path and with nitrogen $N_2$, which is absorption neutral in the comparison beam path, for the adjustment setting of the sensitivity of the gas analyzer 82 for the gas components carbon dioxide $CO_2$ and nitrogen oxide NO to be measured. The gas analyzer 82 includes the infrared radiator source 28, the comparison cuvette 24, the measurement cuvette 20, the calibration cuvette 44; 46, 48 for the first receiver detector 30; 32, 34, the radiation filter 42, and the second receiver detector 36; 38, 40.

The construction and mode of operation of the employed gas analyzer 82, 182, which serves for the quantitative and simultaneous determination of carbon dioxide $CO_2$ gas and nitrogen oxide NO gas is in general described in the reference German Printed Published Patent document DE-OS 3,937,141 and U.S. Pat. No. 5,055,688. Two separate light beams of the infrared radiator 28 penetrate alternatingly the two cuvettes 20 and 24 in their longitudinal direction and impinge subsequently onto the calibration cuvette 44, onto the receiver detector 30 for carbon dioxide $CO_2$ gas, and onto the radiation filter 42, and the receiver detector 36 for nitrogen oxide NO gas, in this sequence. For this purpose, the cuvettes passed through by the light beam are furnished with windows open in beam direction, where the windows are transparent to infrared radiation.

Two amplifiers 58 and 60 for the pneumatic signals received from the receiver detectors 30 and 36 are connected to deliver amplified signals to a display 62 for the measured concentrations total carbon (TC) minus total inorganic carbon (TIC) and a display 64 for the measured concentrations total nitrogen (TN).

The chambers 32, 34; 38, 40 of the radiation receiver detectors 30 and 36, disposed sequentially in beam direction, are filled with the gas carbon dioxide $CO_2$ or, respectively, nitrogen oxide NO to be determined in each case. The gas volumes enclosed in the cheers 32, 34; 38, 40 are warmed to varying degrees by absorption of the light beams penetrating the chambers 32, 34; 38, 40. A higher pressure is generated in the front chamber 32; 38 as compared to the rear chamber 34; 40. The pressure difference occurring is transformed into electric voltage variations with the aid of a membrane capacitor 78, 80, where the membrane capacitor 78, 80 is indicated in FIG. 1 by the capacitor symbol, and is measured by a first electrical amplifier 58 or, respectively, by a second electrical amplifier 60 and amplified. The output value of current or voltage of the amplifier 58, 60 is displayed with an electrical display instrument 62, 64. The output value of the first amplifier 58 or, respectively, of the second amplifier 60 is a measure for the carbon dioxide $CO_2$ concentration or, respectively, of the nitrogen oxide NO concentration in the measurement gas 22.

An electrical display instrument 62, 64 is connected downstream of each output of the amplifier 58, 60 for displaying the electrical output value of the amplifier 58, 60, where the electrical output value of the amplifier 58, 60 represents a measure for the difference pressure signal of the respective receiver detectors 30, 36, as further indicated in the German Printed Patent document DE-OS 3,937,141, column 2, lines 54–58.

Figure 2:
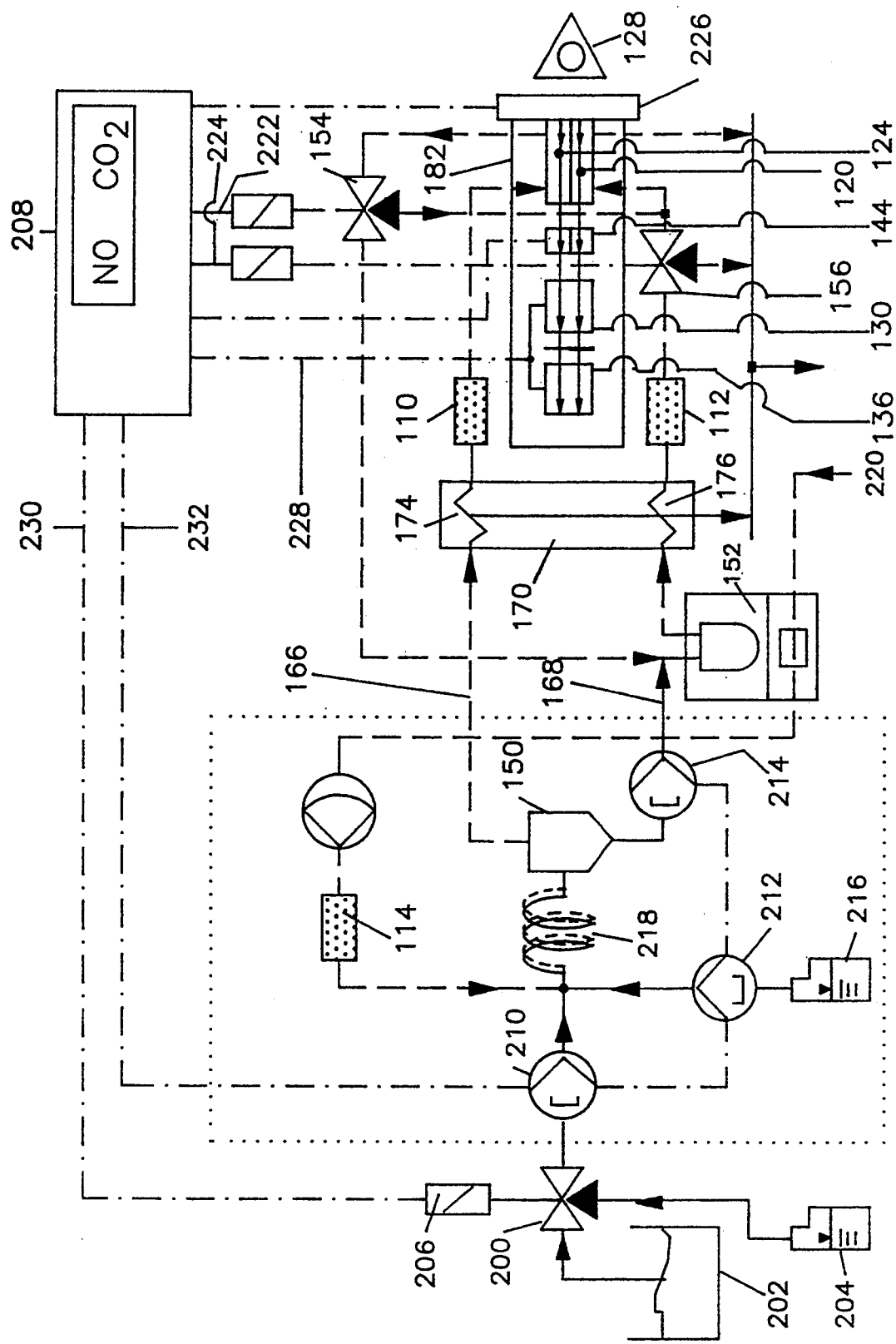
FIG. 2 shows a more detailed schematic diagram of a method for measuring the total content of organic carbon and of nitrogen in water.

FIG. 2 shows a more detailed configuration of a second embodiment, configured similar to the embodiment of FIG. 1. The individual components employed according to the FIG. 2 can be found in comparable sections described in connection with FIG. 1.

The apparatus for analyzing simultaneously organic carbon and nitrogen according to FIG. 2 comprises a phase separator 150 having an input, a first output, and a second output. A first cooler 174 of a double cooler 170 has an input connected to the first output of the phase separator 150 and has a gas output. A first cuvette or comparison cuvette 124 has a gas input connected to the gas output of the first cooler 174 and has an output. A first valve 154 has an input connected to the output of the comparison cuvette 124 and has a first output and a second output. A thermal reactor 152 has a first input connected to the first output of the first valve 154 and has a second input connected to the second output of the phase separator 150 and has an output. A second cooler 176 of the double cooler 170 has an input connected to the output of the thermal reactor 152 and has an output. A second valve 156 has an input connected to the output of the second cooler 176 and has a first output and a second output. A second cuvette or measurement cuvette 120 has an input connected to the output of the second valve 156 and has an output. An infrared radiator source 128 provides an infrared radiation to the first cuvette 124 and to the second cuvette 120. A chopper wheel 226 is disposed between the infrared radiator source 128 and the comparison cuvette 124 and the measurement cuvette 120. A calibration cuvette 144 has a first chamber filled with a neutral gas, where the first chamber is disposed downstream of the comparison cuvette 124 in beam direction. The calibration cuvette has a second chamber filled with a calibration gas, where the second chamber is disposed downstream of the measurement cuvette 120 in beam direction. A first receiver detector 130 is disposed downstream of the calibration cuvette 144 in beam direction and has an output.

A radiation filter can be disposed following to the first receiver detector in radiation direction and a second receiver detector can be disposed following to the radiation filter in radiation direction and having an output. A first amplifier having an input connected to the output of the first receiver detector and having an output can be incorporated in the control display 208. A second amplifier having an input connected to the output of the second receiver detector and having an output can be incorporated in the control display 208. The control display can include a first display having an input connected to the output of the first amplifier and a second display having the input connected to the output of the second amplifier.

A first control line 228 can provide a connection between the first receiver detector 130, the second receiver detector 136, and the control display 208.

As shown in FIG. 2, a first connection is provided between the second output of the first valve 154 and the input of the measurement cuvette 120, and a second connection is provided between the output of the measurement cuvette 120 and a second input of the second valve 156. A discharge is located in the second connection.

A third valve 200 is connected to a sample probe source 202 and to a zero probe source 204. A relay 206 of the third valve is connected by a second control line 230 to the control display 208. A first membrane pump 210 has a control input, an input, and an output. The input of the first membrane pump 210 is connected to the third valve 200. The control input of the first membrane pump 210 is connected by a third control line 232 to the control display 208. A second membrane pump 212 has an input connected to a source for acid 216 and has an output and a control input connected to a control output of the first membrane pump 210 and has a control output. A separating column 218 has an input connected to the output of the first membrane pump 210 and to the output of the second membrane pump 212 and an output connected to the phase separator 150. A third membrane pump 214 has an input connected to the second output of the phase separator 150 and has an output connected to an input of the thermal reactor 152 and a control input connected to the control output of the second membrane pump 212.

An air feed 220 is provided through the thermal reactor 152 having an air output. A first gas filter 114 has an input connected to the air output of the thermal reactor 152 and has an output connected to the input of the separating column 218.

A first control connection 222 is furnished between the first valve 154 and the control display 208 and a second control connection 224 is furnished between the second valve 156 and the control display 208.

A second gas filter 110 is disposed between the output of the first cooler 174 and the input of the first cuvette 124. A third gas filter 112 is disposed between the output of the second cooler 176 and the input of the second cuvette 120.

The mode of operation of the invention is as follows:

A sample of the water to be analyzed passes into the phase separator 50, wherein the phase separator 50 separates the inorganic carbon component part TIC from the sample, transforms and reacts this part into carbon dioxide $CO_2$ gas, and feeds the carbon dioxide $CO_2$ gas via the line 66 to the double cooler 70. The main amount of the water vapor is removed from the carbon dioxide $CO_2$ gas by condensation in the double cooler 70. The carbon dioxide $CO_2$ gas, thus dried at a temperature of about 4° C., passes as a comparison gas C into the comparison cuvette 24. Then, the dried carbon dioxide gas passes through the comparison cuvette 24. The dried carbon dioxide $CO_2$ gas passes from the comparison cuvette 24 through the non-activated valve 54 into the thermal reactor 52.

If the connections of the three-way valves 54 and 56, respectively, are designated beginning in FIG. 1 at the left and going in a clockwise direction with 1, 4 for <, 2, 5 for >, and with 3, 6 for ∧, then the connection 1–2 represents the gas path during non-activation of valve 54.

If the valve 54 is activated, then a gas path exists from port 2 through port 3. If the valve 56 is activated, then a gas path exists from port 4 to port 6. The flow direction of the gases is indicated by the arrow direction, indicated in the respective connection lines.

The dried carbon dioxide $CO_2$ gas is oxidized in the thermal reactor 52 together with the liquid part of the sample, fed from the phase separator 50 via the line 68, to carbon dioxide $CO_2$ and nitrogen oxide NO.

A thermal reactor is described in the reference German Printed Patent document DE-OS 2,322,293 and U.S. Pat. No. 3,814,583 on page 4. A reaction vessel is shown, where continuously water is fed via line 1 to the reaction vessel 2 and where air is fed via line 2 to the reaction vessel 2. The water is evaporated at a temperature of about 900° C. and the carbon present in the water is oxidized with the oxygen present in the air to carbon dioxide $CO_2$.

The gaseous oxidation product of the sample, designated in the following as "the gas sample," contains the total carbon part and nitrogen part of the sample of the water to be analyzed. A substantial part of the water vapor is removed from the gas sample through condensation at the same temperature of about 4° C. in the double cooler 70. The dried gas sample passes through the non-activated valve 56 as a measurement gas 22 into the measurement chamber 20 of a gas analyzer 82, 182.

Since the comparison gas 26 contains carbon dioxide $CO_2$, where the concentration of the carbon dioxide $CO_2$ corresponds to the actual inorganic carbon component part TIC of the sample, there is generated in the first receiver detector 30, sensitized to carbon dioxide $CO_2$, a pneumatic signal.

The mode of operation of the pneumatic receiver detectors 30 and 36 is described in more detail in the reference German Printed Patent document DE-OS 3,937,141 and U.S. Pat. No. 5,055,688. The embodiment illustrated in FIG. 2 of the German Printed Patent document DE-OS 3937141 shows an analyzer with two receiver detectors disposed in series in beam direction. The first receiver is filled with carbon monoxide CO gas for the determination of the carbon monoxide CO concentration of a gas sample, and the rearward, second receiver is filled with carbon dioxide $CO_2$ gas and serves for the determination of the carbon dioxide $CO_2$ concentration of the same gas sample. The generation of a difference pressure and the operation of transforming the difference pressure into an electrical signal is performed with the aid of a membrane capacitor indicated in FIG. 1 by the capacitor symbol.

Said pneumatic signal corresponds to the difference of the concentration value for the total carbon TC minus the concentration value for the total inorganic carbon TIC. This difference value, total carbon TC minus total inorganic carbon TIC, is displayed through the amplifier 58 on display 62. At the same time, a pneumatic signal is generated in the receiver detector 36. The pneumatic signal of the receiver detector 36 corresponds to the concentration value of the desired nitrogen part TN, displayed by amplifier 60 on display 64.

The cross-sensitivities versus water vapor, occurring during the measurement of nitrogen oxide NO, can only be in part eliminated by condensation of the gases in the upstream-disposed double cooler 70. It is possible to set the measurement gas 20 and the comparison gas 26 to the same low water vapor content by the step that the measurement gas 22 and the comparison gas 26 are simultaneously led through the same double cooler 70 and are cooled at the same temperature, such that the cross-sensitivities occurring in the measurement cuvette 20 and the comparison cuvette 24 are compensated and balanced and the pneumatic signals in the receiver detector 36 correspond to the undistorted and uncorrupted nitrogen oxide NO concentration value of the gas sample.

The zero point and the sensitivities of the measurement device are subjected to various influences. Aging and water vapor cross-sensitivities of the gas analyzer 82, 182 as well as a sensitivity influence by the inorganic carbon dioxide $CO_2$ part, caused by the measurement principle with a flowing comparison gas 26, belong to these influences. The inorganic carbon dioxide $CO_2$ part can influence the sensitivity depending on the concentration up to several 100%. In order to eliminate these influence effects, the measurement device is balanced as follows sequentially after predetermined time intervals.

The following describes the adjustment of the measurement device.

The gas sample taken from the phase separator is fed through the gas line 66 and through the first cooler 74 of the double cooler 70 to the comparison cuvette 24 and, upon activation of the valve 54 passing from port 2 to port 3 of the valve 54, as well as by activation of the valve 56 passing from port 4 to port 6, first toward the measurement cuvette 20 and then to the discharge port 72. The downward arrow starting at the measurement cuvette 20 of FIG. 1 represents the gas discharge port 72. The gas discharge port can be a simple opening in a gas line, which releases the gaseous parts of the sample into the environment. The valve 56 can also be disposed in front of the double cooler 70 such that the gas sample also passes over the second cooler 76 of the double cooler 70. The influences changing the zero point are balanced with this adjustment setting and with the aid of electronic means in the amplifiers 58 and 60. Then, the calibration cuvette 44 is slid into the beam path between the measurement cuvette 20 and the comparison cuvette 24 and the receiver detectors 30 and 36, and the sensitivity for the carbon dioxide $CO_2$ channel and the nitrogen oxide NO channel is set corresponding to the calibration gases disposed in the calibration cuvette 44. The calibration cuvette 44 can contain carbon dioxide $CO_2$, nitrogen oxide NO, or a mixture of carbon dioxide $CO_2$ and nitrogen oxide NO. The calibration can be performed by a plurality of sequential measurements with differently filled calibration cuvette 44. This setting takes also into consideration the influence of the actual inorganic carbon dioxide concentration in addition to apparatus aging and soiling, and correctly shows the total organic carbon content TOC value of the sample as sum of the volatile, dissolved and solid materials. It is an advantage that no zero liquid or calibration gas is required for this balancing step.

In addition to the above described method for the adjustment for the measurement device, there is also to be performed a calibration of the total measurement device. In this case, modules such as pumps are also taken into consideration in the calibration of the total measurement device. This calibration is performed without a zero defining liquid. The calibration of the zero point and of the sensitivity is performed with a calibration liquid fed to the phase separator 50, which contains a known concentration of organic carbon and of nitrogen compounds. The calibration liquid is fed as sample to the phase separator 50. According to a first step, the zero point and the sensitivity of the device are set according to the above described adjustment based on the activation of the valves 54 and 56. According to a second step, these valves 54 and 56 are deactivated. The receiver detectors 30 and 36 deliver in each case a pneumatic signal, which corresponds to the known concentration of organic carbon and of nitrogen compounds. The sensitivity of the downstream disposed amplifiers 58 and 60 are set with electronic means based on the thus generated signals. After termination of the calibration process, the device is reset again to the measurement operation for measuring the samples taken from the water to be analyzed.

A balancing process with the sample of the water, as described above, can follow immediately to the calibration of the measurement device in order to establish the reference to the organic carbon dioxide $CO_2$ content of the sample.

It is advantageous to perform the balancing process more frequently, for example, every two to twelve hours, whereas the calibration process with the calibration liquid should be performed, dependent on the measurement conditions, only every 2 to 24 days or repeated after even longer time intervals.

It will be understood that each of the elements described above, or two or more together, may also find a useful application in other types of analytical measurement devices and methods differing from the types described above.

While the invention has been illustrated and described as embodied in the context of a method for the measurement of the total content of organic carbon and nitrogen in water, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for the simultaneous analysis of total content of organic carbon and nitrogen from an aqueous sample comprising
    a phase separator having an input for receiving an aqueous sample, a first output, and a second output;
    a double cooler including a first cooler and a second cooler, wherein;
        the first cooler of the double cooler has an input connected to the first output of the phase separator and has a gas output;
    a first cuvette having a gas input connected to the gas output of the first cooler and having an output;
    a first valve having an input connected to the output of the first cuvette and having a first output and a second output;
    a thermal reactor having a first input connected to the first output of the first valve and having a second input connected to the second output of the phase separator and having an output; wherein the
        second cooler of the double cooler has an input connected to the output of the thermal reactor and having an output;
    a second valve having an input connected to the output of the second cooler and having a first output, and a second output;
    a second cuvette having an input connected to the first output of the second valve and having an output;
    an infrared radiator source providing an infrared radiation to the first cuvette and to the second cuvette;
    a chopper wheel disposed between the infrared radiator source and the first cuvette and the second cuvette;
    a calibration cuvette having a first chamber filled with a gas disposed after the first cuvette in beam direction and having a second chamber filled with a calibration gas disposed after the second cuvette in beam direction;
    a first receiver detector disposed neighboring to the calibration cuvette in beam direction and having an output;
    a radiation filter disposed following to the first receiver detector in radiation direction;
    a second receiver detector disposed neighboring to the radiation filter in radiation direction and having an output;
    a first amplifier having an input connected to the output of the first receiver detector and having an output;
    a second amplifier having an input connected to the output of the second receiver detector and having an output;
    a first display having an input connected to the output of the first amplifier and disposed in a control display;
    a second display having the input connected to the output of the second amplifier and disposed in the control display.

2. The apparatus according to claim 1, further comprising
    a first connection between the second output of the first valve and the input of the second cuvette;
    a second connection having a discharge and disposed between the output of the second cuvette and the second output of the second valve.

3. The apparatus according to claim 1, further comprising
    a sample probe source;
    zero sample source;
    a third valve connected to the sample probe source and connected to the zero probe source;
    a relay of the third valve connected by a second control line to the control display;
    a first membrane pump having an input connected to the third valve and having an output, a control output and a control input;
    a third control line connecting the control input of the first membrane pump to the control display;
    a source for acid;
    a second membrane pump having an input connected to the source for acid and having an output and having a control input connected to the control output of the first membrane pump and having a control output;
    a separating column having an input connected to the output of the first membrane pump and to the output of the second membrane pump and having an output connected to the phase separator;
    a third membrane pump having an input connected to the second output of the phase separator and having an output connected to an input of the thermal reactor and having a control input connected to the control output of the second membrane pump.

4. The apparatus according to claim 3, further comprising
    an air feed through the thermal reactor having an air output;
    a first gas filter having an input connected to the air output of the thermal reactor and having an output connected to the input of the separating column.

5. The apparatus according to claim 1, further comprising
    a first control signal connection between the first valve and the control display;
    a second control signal connection between the second valve and the control display.

6. The apparatus according to claim 1, further comprising
    a second gas filter disposed between the output of the first cooler and the input of the first cuvette;
    a third gas filter disposed between the output of the second cooler and the input of the second cuvette.

7. The apparatus according to claim 1, further comprising
    a first control line providing a connection between the first receiver detector, the second receiver detector, and the control display.

* * * * *